US012710420B2

(12) United States Patent
Wetzel et al.

(10) Patent No.: US 12,710,420 B2
(45) Date of Patent: Aug. 18, 2026

(54) VELVET DISEASE DETECTION DEVICE, SYSTEM AND METHOD

(71) Applicant: MOTE MARINE LABORATORY, INC., Sarasota, FL (US)

(72) Inventors: Dana L. Wetzel, Sarasota, FL (US); Tracy Sherwood, Sarasota, FL (US)

(73) Assignee: MOTE MARINE LABORATORY, INC., Sarasota, FL (US)

( * ) Notice: Subject to any disclaimer, the term of this patent is extended or adjusted under 35 U.S.C. 154(b) by 977 days.

(21) Appl. No.: 17/865,718

(22) Filed: Jul. 15, 2022

(65) Prior Publication Data

US 2023/0003728 A1 Jan. 5, 2023

Related U.S. Application Data

(63) Continuation-in-part of application No. 17/244,636, filed on Apr. 29, 2021, now abandoned.

(60) Provisional application No. 63/017,540, filed on Apr. 29, 2020.

(51) Int. Cl.
*G01N 33/543* (2006.01)
*B01L 3/00* (2006.01)
*G01N 33/569* (2006.01)

(52) U.S. Cl.
CPC ...... *G01N 33/54386* (2013.01); *B01L 3/5085* (2013.01); *G01N 33/56905* (2013.01); *B01L 2300/023* (2013.01); *B01L 2300/024* (2013.01); *B01L 2300/025* (2013.01); *B01L 2300/0636* (2013.01); *G01N 2800/26* (2013.01)

(58) Field of Classification Search
CPC ....... G01N 33/54386; G01N 33/56905; G01N 2800/26; G01N 33/543; B01L 3/5085; B01L 2300/023; B01L 2300/024; B01L 2300/025; B01L 2300/0636; C12N 2310/16; C12N 15/115; Y02A 40/81
USPC ........................................................ 435/287.2
See application file for complete search history.

(56) References Cited

U.S. PATENT DOCUMENTS

| | | | | |
|---|---|---|---|---|
| 9,121,849 B2 | 9/2015 | Babu | | |
| 2006/0003322 A1* | 1/2006 | Bentwich | G16B 15/10 | 435/6.16 |
| 2013/0210025 A1* | 8/2013 | Babu | G01N 33/5308 | 435/6.19 |

FOREIGN PATENT DOCUMENTS

WO 2018147077 A1 8/2018

OTHER PUBLICATIONS

Lieke, T. et al. (2020). "Sustainable aquaculture requires environmental-friendly treatment strategies for fish diseases." Reviews in Aquaculture. 12. 943-965. (Year: 2020).*

Donzeau, M., Knappik, A. (2007). Recombinant Monoclonal Antibodies. In: Albitar, M. (eds) Monoclonal Antibodies. Methods in Molecular Biology, vol. 378. Humana Press. (Year: 2007).

(Continued)

*Primary Examiner* — Charles Capozzi
*Assistant Examiner* — Jacqueline Brazin
(74) *Attorney, Agent, or Firm* — BURR & FORMAN

(57) ABSTRACT

Velvet disease infestation is detected using affinity reagents that are cross-reactive with one or more *A. ocellatum* or *P. pillulare* antigens. The analysis may be performed shipboard, dockside, in an aquaculture or aquarium setting, otherwise in situ at the point of sample collection or elsewhere. The results may be used to monitor health and disease of captured or cultured fish species or the safety of water to be introduced into an aquaculture facility.

20 Claims, 5 Drawing Sheets

(56) References Cited

OTHER PUBLICATIONS

Lieke et al., "Sustainable Aquaculture Requires Environmental-friendly Treatment Strategies for Fish," Diseases. Rev. Aquac., 2019, pp. 1-23.

Levy et al., "A Highly Specific PCR Assay for Detecting the Fish Ectoparasite *Amyloodinium ocellatum*," Dis. Aquat. Org., 2007, 73(3):219-226.

Smith et al., "Development of an Enzyme-Linked Immunosorbent Assay (ELISA) for the Detection of Antibody to the Parasitic Dinoflagellate *Amyloodinium ocellatum* in *Oreochromis aureus*," Vet. Parasitol., 1992, 42(1-2):145-155.

* cited by examiner

VELVET DISEASE DETECTION DEVICE, SYSTEM AND METHOD

CROSS-REFERENCE TO RELATED APPLICATION

This application is a continuation-in-part of U.S. patent application Ser. No. 17/244,636 filed Apr. 29, 2021 and entitled "VELVET DISEASE TEST AND METHOD", which claims priority to U.S. Provisional Application No. 63/017,540 filed Apr. 29, 2020 and entitled "VELVET DISEASE DETECTION DEVICE, SYSTEM AND METHOD", the disclosures of which are incorporated herein by reference.

TECHNICAL FIELD

This invention relates to fish harvesting, testing and aquaculture.

BACKGROUND

One of the most prominent challenges in aquaculture for safe production and maintaining the welfare of animals is control of infectious diseases. In aquaculture, there is up to a 50% of production loss caused by infectious diseases, resulting in multibillion-dollar annual losses. The result is significant epidemics in fish and great financial loss to the associated industries. Besides bacterial, fungal and viral diseases, parasites can significantly harm finfish aquaculture enterprises. Although normally present in almost all ecosystems, parasites are generally benign for healthy fish. However, parasites can become a problem under stressful conditions inherently found in aquaculture. In order to maximize aquaculture productivity, high stocking densities and less than ideal water quality are common and provide optimal conditions for the infestation of parasites.

Dinoflagellates are a diverse group of aquatic protozoans and some members are parasitic, infesting the skin and gills of marine organisms. Amyloodiniosis, caused by *Amyloodinium ocellatum* (AO) in temperate and tropical marine fish is one of the most common and devastating parasitic diseases. Although less common and less pathogenic, Piscinoodiniosis, caused by *Piscinoodinium pillulare* (PP), is the freshwater version of AO in temperate and tropical freshwater fish and has convergent evolution with AO. Both are responsible for "velvet disease", and are economically problematic in the fish aquaculture industries due to their ability to reproduce large numbers of infectious agents quickly and due to difficult 4925ies in detecting such agents before the onset of morbidity and mortality. In enclosed systems, such as recirculation aquaculture systems (RAS) or aquariums, these parasites can rapidly reproduce and cause catastrophic mortalities in fish and elasmobranchs.

Most parasitic species infect invertebrates, but those belonging to the genera *Amyloodinium* and *Piscinoodinium* infest the skin and gills of susceptible marine, brackish, or freshwater fish causing velvet disease. Velvet disease infestation causes damage to the host fish through the parasite rhizoids that penetrate deep into the epithelial cells of the skin and gills to obtain nutrition leading to cell death. Infections and mass mortalities of marine fish in tropical aquaria by AO have been documented since the 1930s across nearly every teleost taxa investigated. Essentially all fish within the wide environmental range of velvet disease are highly susceptible to a lethal infection when kept in captivity. The exact economic impact of AO is unclear, but once a facility has become infected, a large portion of the fish may succumb before the infection can be tamed. Eradication of velvet disease is both time consuming and costly and may prevent a business from becoming financially successful.

Velvet disease lifecycle consists of three main stages: trophant (parasitic, feeding stage), tomont (encysted, reproductive stage), and dinospore (free-swimming, infective stage). The trophants firmly anchor to the fish and feed on its epithelia by means of rhizoids. After feeding for 4-5 days (temperature dependent) and growing in size from ~12 um to 100 um, trophants loosen their attachment and drop from the fish. They then encyst on the substratum, transform to tomonts, and start dividing. Reproduction peaks in a few days (again temperature dependent) with the release of as many as 256 infective, highly motile dinospores from each tomont. Upon finding a teleost host, the dinospores begin the lifecycle again. Dinospores remain infective for at least a week, with evidence that lower temperatures and non-piscine hosts may be exploited to prolong survival for up to a month. Dinospores have even been found to survive freezing temperatures and can be aerosolized over a distance of 2.5 m or more. Since the lifecycle can be completed in as little as 3 days at 20° C., parasite load can increase rapidly and cause severe, acute mortality, and infections that are both very difficult to remove and control.

Mortalities from both AO and PP parasites are usually attributed to anoxia, associated with serious gill hyperplasia, inflammation, hemorrhage and necrosis in heavy infestations; or with osmoregulatory impairment and secondary microbial infections due to severe epithelial damage in mild infestation, see e.g., Moreira et al., *Physiological responses of reared sea bream* (*Sparus aurata Linnaeus,* 1758) *to an Amyloodinium ocellatum outbreak*, J Fish Dis. 2017 November; 40(11):1545-1560. This disease state, common in many cultured fish, is contagious, spreads rapidly and has high mortality. Behavioral and physical changes can sometimes be seen just prior to death including flashing, rubbing, gasping at the surface, and a velvety appearance of the skin. However, due to its rapid onset, there are often no signs of infection before mortalities begin to appear within a system, making it imperative to diagnose and treat as early as possible Transmission of velvet disease can be through direct contact with live dinospores via contaminated fish or water, including aerosolized droplets from one culture system to another, through fomites (nets, hands, shoes, equipment, etc.), wildlife, dead fish, biofilms on tank and plumbing surfaces, and even from infected frozen baitfish used as feed. Furthermore, the potential for spreading infectious pathogens is increasing due to enhanced capabilities for the transportation of live, and possibly infected fish, into other aquaculture farms and systems.

Specific polymerase chain reaction (PCR) assays to detect ribosomal DNA and a loop mediated isothermal amplification (LAMP) assay for *Amyloodinium dinoflagellate* identification has been developed, see e.g., Picón-Camacho et al., *Development of a rapid assay to detect the dinoflagellate Amyloodinium ocellatum using loop-mediated isothermal amplification* (*LAMP*), Vet Parasitol. 2013 Sep. 23; 196(3-4):265-71. The assays perform equally well in a simple artificial seawater medium and in natural seawater containing a plankton community assemblage and are not inhibited by gill tissue. However, this detection technique employs a clinical setting, appropriate laboratory equipment and expertise to carry out the diagnostic assays, something that most aquaculture farms will not have.

Because AO can tolerate a wide range of salinities (2 to 50 ppt) and temperatures (15-30° C.), manipulations of potential adverse environmental conditions may stop divisions, but they will not kill or control outbreaks of the parasite. Under current chemical mitigation options, only the dinospore life stage is susceptible to drug treatment. Using dip/bath treatments of freshwater, formalin or hydrogen peroxide on afflicted fish can force attached trophonts to detach, transform into the reproductive tomont cyst, and finally into the free-swimming dinospores that can then be killed using 0.15-0.2 mg/L free copper ion for 2-3 weeks. However, treatments must be repeated multiple times or for a prolonged period to control infection. It is important during treatment to carefully monitor copper concentration, as copper is lethal to fish at higher concentrations and if allowed to drop below lethal levels for dinospores, fish can quickly become re-infected with the copper tolerant trophont stage. While effective, freshwater dips or formalin baths, followed by copper treatment, are too harsh to utilize on highly infected or young sensitive fish and are very costly in terms of both time and treatment. Chloroquine is also an effective treatment strategy, but it can only be used on non-food fish. Current best practice may employ freshwater dips followed by numerous tank transfers allowing infected tanks to be thoroughly dried or disinfected between transfers. Drawbacks to this approach include high cost for labor and time, and frequent handling and consequent extreme stressful for the fish. These strict, costly, and time-consuming protocols are however necessitated by the significant economic consequences from an infestation introduced into a closed system.

Opportunistic parasites play a critical role in influencing the productivity, sustainability and economic viability of global finfish aquaculture enterprises. Without stringent and appropriate control measures, the impacts of these pathogens can often be significant. As global aquaculture continues to expand, the spread of parasites to new environments, and the occurrence and the severity of infestations from parasites, may also rise along with the economic fallout from such infections. The potential for climate change affecting environmental conditions may also affect current production practices, interactions between wild and farmed aquatic stocks, parasite life cycles and transmission pathways. These and other pressures may consequently further constrain production, sustainability and economic feasibility.

There remains an unmet need for an in-situ rapid diagnostic test (RDT) biosensor to be used by the farmers for the early detection of infection and increased viability of fish in the aquaculture industry.

SUMMARY

The most common diagnostic technique used for identifying infections from AO and PP parasites is by microscopic analyses of mucus, skin and gills. However, there are several impediments to relying on microscopy for monitoring presence of these parasites. First, the identification of the parasites can be subjective, leading to potential false positives/negatives and second, by the time there is visual or behavioral evidence suggesting the possible onset of disease, it is too late for effective treatment and control. A tank-side RDT could ameliorate these impediments by providing growers a biosensor for early detection of these parasites.

Current methodologies for the detection of AO and PP are insufficient to circumvent outbreaks that can occur extremely rapidly, and which can lead to 100% mortality within a few days. Control is most successful when a diagnosis is made while the parasite load is still low. However, the trophonts must be numerous for a robust determination, which means that it may well be too late for effective treatment strategies. Some fish have been found to develop a specific, antibody-mediated response to AO. Unfortunately, since immune response is slow to develop, host antibody-based tests are not useful in early detection of infection.

AO and PP parasites do not move directly from fish to fish as their immediate mode of transmission, and instead first pass through a developmental phase in the water when not attached to a fish host. While trophonts can contaminate an aquaculture system via an infected host fish, both tomonts and infective dinospores can be introduced directly with incoming seawater, becoming a separate source of infection for fish in the system. Consequently, assessing the presence of both trophonts on fish gill and skin tissue, and infective tomonts and dinospores in the water, will provide a more comprehensive monitoring scheme for the early detection and prevention of velvet disease. Preferably this involves early detection or identification of infected water or fish prior to introducing either into a closed water system. An RDT biosensor could provide a rapid in-situ low cost alternative for the detection of AO. With a parasite that reproduces as rapidly as velvet disease, immediate tank-side diagnosis is critical.

Disclosed herein are devices, systems and methods employing affinity reagents, such as recombinant monoclonal antibodies (rmAbs) and other affinity reagents discussed below, selected to target the two infectious life stages of AO, PP, or AO and PP. The disclosed device, system and method may be used with a variety of sample sources, and may use an RDT biosensor for detection of AO or PP. The samples may, for example, be taken from any naturally occurring or manmade water source or site where fish are reared, housed or wild-caught, and may for example represent water samples taken from an aquaculture water source; water samples taken from an aquaculture facility (e.g., a pond, pen, tank, cage or other fish-rearing enclosure); samples taken from aquaculture effluent; samples taken from fishing vessels (e.g., water samples taken from holding tanks or from seawater); or samples taken from fish (e.g., as fish mucus, fish gill swabs, skin swabs, fish tissue, fish tissue extracts or fish mucus extracts).

Accordingly, in one aspect the present invention provides a device for detecting velvet disease infestation in aquaculture and fishing, the device comprising a test plate comprising a support bearing at least one conjugated (detection) affinity reagent and at least one immobilized (capture) affinity reagent that are cross-reactive with one or more AO or PP antigens, the affinity reagents being bound to the support or bound to particles that can migrate along the support. The device may be used to detect AO or PP antigens in the above-described samples. In embodiments, the affinity reagents may be a protein or peptide, a sequence of nucleic acids, such as an aptamer, or another small molecule. In embodiments, the affinity reagents may be antibodies or similar compounds, such as natural antibodies, synthetic antibodies, polyclonal antibodies, monoclonal antibodies, recombinant antibodies, including recombinant monoclonal antibodies (rmAbs), or "chemical antibodies," including aptamers and other oligos of nucleotides.

In another aspect the present invention provides a device for detecting velvet disease infestation in aquaculture and fishing, the device comprising a test plate comprising a support bearing i) a sample taken from an aquaculture water source, aquaculture facility, aquaculture effluent or fish and ii) at least one conjugated (detection) affinity reagent and at least one immobilized (capture) affinity reagent plate that are cross-reactive with one or more velvet disease antigens, the affinity reagent being bound to the support or bound to particles that can migrate along the support.

In another aspect the present invention provides a system for assessing the presence or absence of velvet disease infestation in aquaculture and fishing, the system comprising a test plate comprising a support bearing i) a sample taken from an aquaculture water source, aquaculture facility, aquaculture effluent or fish and ii) at least one conjugated (detection) affinity reagent and at least one immobilized (capture) affinity reagent that are cross-reactive with one or more AO or PP antigens, the affinity reagents being bound to the support or bound to particles that can migrate along the support; and a detector configured to detect the absence or presence of one or more AO or PP antigens in such sample based on the extent to which such AO or PP antigens become or do not become bound to such conjugated affinity reagents.

In yet another aspect the present invention provides a system for assessing the presence or absence of velvet disease infestation in aquaculture and fishing, the system comprising a test plate comprising a support bearing i) a sample comprising one or more AO or PP antigens in solution and ii) at least one conjugated (detection) affinity reagent and at least one immobilized (capture) affinity reagent that are cross-reactive with one or more such AO or PP antigens, the affinity reagents being bound to the support or bound to particles that can migrate along the support; a detector configured to detect the absence or presence of velvet disease antigens in such sample based on the extent to which such antigens become or do not become bound to such conjugated affinity reagents; a processor; storage for a set of sample locations, sample dates and measured velvet disease presence for such samples; and an engine for detecting AO and PP antigens in any one or more such samples.

In another aspect the present invention provides a method for assessing the presence or absence of velvet disease infestation in aquaculture and fishing, the method comprising the steps of obtaining a sample from an aquaculture water source, aquaculture facility, aquaculture effluent or fish, contacting a test plate with the sample, the test plate comprising a support bearing at least one conjugated (detection) affinity reagent and at least one immobilized (capture) affinity reagent that are cross-reactive with one or more AO or PP antigens, the affinity reagents being bound to the support or bound to particles that can migrate along the support; and providing either a positive or negative detection of velvet disease infestation based on the extent to which AO or PP antigens that may be in such sample become or do not become bound to such conjugated affinity reagents.

In embodiments, the affinity reagents may be a protein or peptide, a sequence of nucleic acids, such as an aptamer, or another small molecule. In embodiments, the affinity reagents may be antibodies or similar compounds, such as natural antibodies, synthetic antibodies, polyclonal antibodies, monoclonal antibodies, recombinant antibodies, including recombinant monoclonal antibodies (rmAbs), or "chemical antibodies," including aptamers and other oligos of nucleotides.

An especially desirable embodiment of the disclosed device, system and method will permit testing to be performed on board a ship, at dockside, or in an aquarium, aquaculture facility, or farm. A further especially desirable embodiment of the disclosed device, system and method will permit testing to be performed on water, fish gill, fish mucus or fish skin swab samples.

The above summary is not intended to describe each illustrated embodiment or every implementation of the subject matter hereof. The figures and the detailed description that follow more particularly exemplify various embodiments.

BRIEF DESCRIPTION OF THE DRAWING

Subject matter hereof may be more completely understood in consideration of the following detailed description of various embodiments in connection with the accompanying figures, in which.

Figure 1:
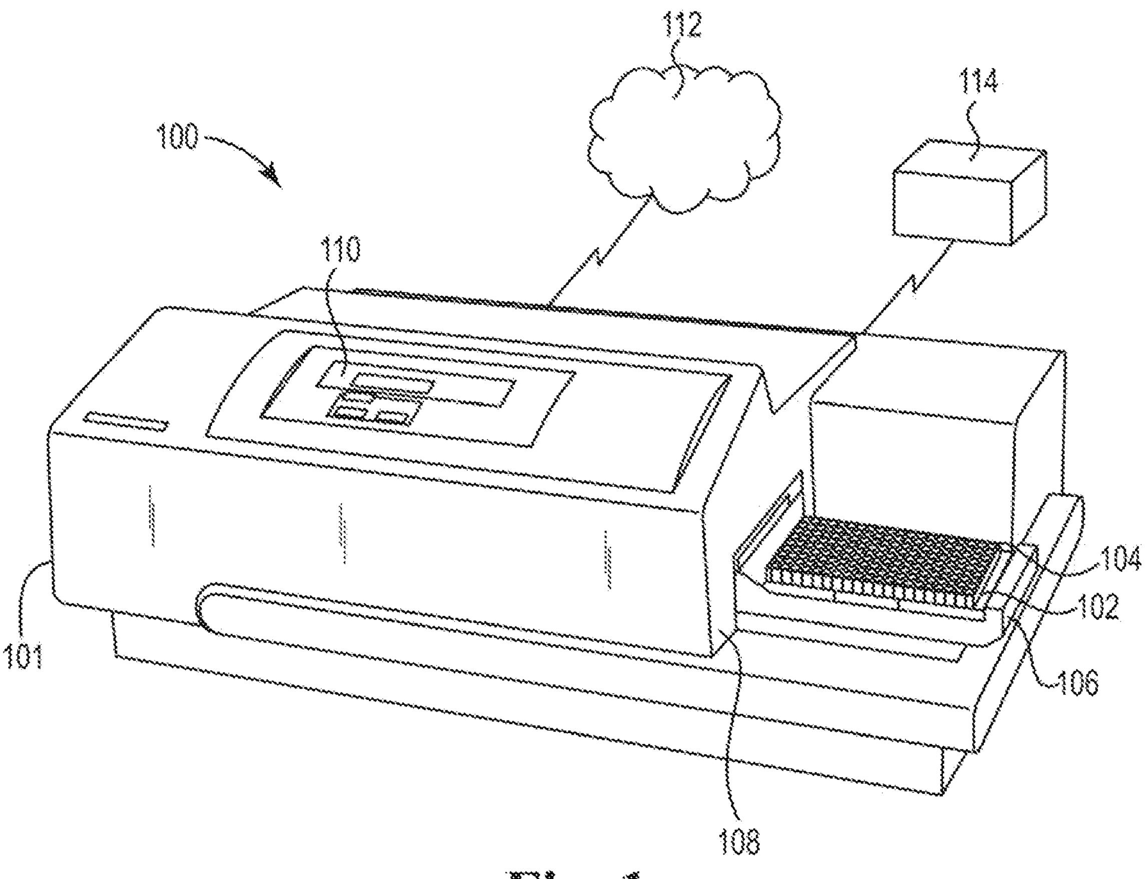
FIG. 1 is a schematic view of a system for assessing and storing velvet disease detection data.

While various embodiments are amenable to various modifications and alternative forms, specifics thereof have been shown by way of example in the drawing and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Velvet disease is problematic in warm water fresh and marine fisheries and aquaculture, due to its ability to rapidly produce large quantities of infectious dinospores, and is hard to detect with current technologies (microscopy) until morbidity and mortality has occurred. At that point treatment and control options are limited, leading to massive loss of fish product and reduced revenue for the growers.

Commercial disease RDT biosensors, such as for *Vibrio cholera*, typically employ a lateral flow technology assay (LFA), based on the principles of immunochromatography and nanotechnology, in which the main components used for detection are antibodies (Abs). Antibody based-biosensors work similarly to enzyme-linked immunosorbent assay (ELISA) where the sensor relies on the ability of the Abs biosensor to recognize its target of interest (the antigen; Ag). An effective Ab-based biosensor should have high specificity in a very complex medium, well-characterized binding properties, high stability, and the potential for low-cost, large-scale production.

Polyclonal Abs (pAbs) are a heterogeneous antibody mixture derived from the immune response in a host animal species, with each pAb recognizing a different structural region (epitope) of the targeted Ag. While these pAbs can be easily generated, batch-related differences, varying affinity and poly-specificity (reactivity with more than one target) can be potential problems. Monoclonal antibodies (mAbs) can be better at targeting a particular region of an Ag of interest, resulting in higher specificity than pAbs; however, animal-derived, cell line production of mAbs can take up to eight months.

Rather than using pAbs or mAbs, an rmAb assay can be selected and developed in vitro using synthetic genes and a targeted selection strategy. Animals are not required, thereby shortening development time, and production can take place in the bacteria *E. coli*, providing a continuous source of Abs (unlike in vivo derived pAbs). Use of rmAbs for antigen binding can also provide improved specificity and high affinity, factors that are especially useful in an RDT biosensor. An assay based on appropriate rmAbs can also optimize the binding of both targets on the various lifestages. Without being bound by theory, rmAbs may provide enhanced cross-reactivity and thus enhanced detection for any of the AO or PP lifestages, allowing for a more thorough and sensitive screening method for fish.

The advantages described here, and many of the examples discussed in greater detail below, focus on rmAbs. Though rmAbs may represent some advantages over pAbs and mAbs, all three fall under the umbrella of affinity reagents. Other affinity reagents include various other proteins and peptides, as well as aptamers and oligos of nucleic acids.

Like recombinant antibodies, aptamers are a non-animal technology and likewise have a rapid development time. Unlike antibodies, aptamers are nucleic-acid based, which often results in a much smaller molecule as they are a short, single-stranded oligo of either DNA or RNA. Despite this difference in material, aptamers share antibodies' ability to bind proteins and modulate their function and are sometimes referred to as "chemical antibodies" due to this antibody-like behavior. Aptamers also share many of the advantages of rmAbs, including exhibiting high specificity and affinity. Aptamers may also exhibit unique advantages in some situations, such as the ability to access hidden epitopes due to their flexibility.

Thus, though the examples discussed herein are discussed primarily in terms of rmAbs, it is to be understood that another affinity reagent may be used while preserving the advantages and functionality of the disclosure as described herein.

Thus the above-described losses from velvet disease may be mitigated by using rmAbs, or another affinity reagent, selected to provide early detection of AO and PP (using, e.g., an RDT employing at least one conjugated (detection) rmAb, or other affinity reagent, and at least one immobilized (capture) rmAb, or other affinity reagent) to test waters or fish present in, or to be introduced into, aquaculture fish farms. Doing so can prevent infection or reinfection, and can permit effective treatment and control before widespread disease occurs.

The HuCAL Human Combinatorial Antibody Libraries from BioRad Laboratories, Inc. is, according to its manufacturer designed for selection and generation of "highly specific, fully human, recombinant monoclonal antibodies in Fab and full immunoglobulin format". However, rather than using HuCAL to generate fully human antibodies, the library may instead be used to generate rmAbs for AO, PP, or AO and PP detection. Doing so does not require the use of animals and can generate useful rmAbs in less than 12 weeks. In contrast to traditional pAbs and mAbs, HuCAL rmAbs are developed in vitro and production occurs in the bacteria *E. coli*. This can provide a continuous source of Abs, unlike in vivo-derived Abs. Further, use of the HuCAL library and rmAb technology can optimize the binding of dinospore and trophont Ags, a distinct advantage over traditional Ab development technology. HuCAL rmAbs may provide enhanced detection for a plurality of parasite life stages, resulting in a more thorough and sensitive screening method for both the trophonts in infected fish, and the trophonts and dinospores in tank water.

Referring now to FIG. 1, representative system 100 for processing and determining the presence of velvet disease is shown. Automated instrument 101 supports a microtiter plate 102 containing sample wells 104 and positioned atop movable stage 106. Once loaded with samples, stage 106 passes into housing 108 where incubation, washing, antibody addition and absorbance measurement steps are performed. Control of the operation of instrument 101 can be performed and the results for selected samples can be displayed using touch panel 110. The results may be stored and processed for analysis using a suitable engine. The term engine as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement a desired functionality, which while being executed may transform a microprocessor system into a special-purpose device. The above-mentioned measurement results may be stored within instrument 101, stored in a nearby or networked separate storage location (not shown in FIG. 1) or remotely stored using for example cloud storage facility 112. The above-mentioned engine may reside within instrument 101, within a nearby or networked separate processing device (not shown in FIG. 1) or may be remotely processed for analysis using for example remote engine and processor 114.

Figure 2:
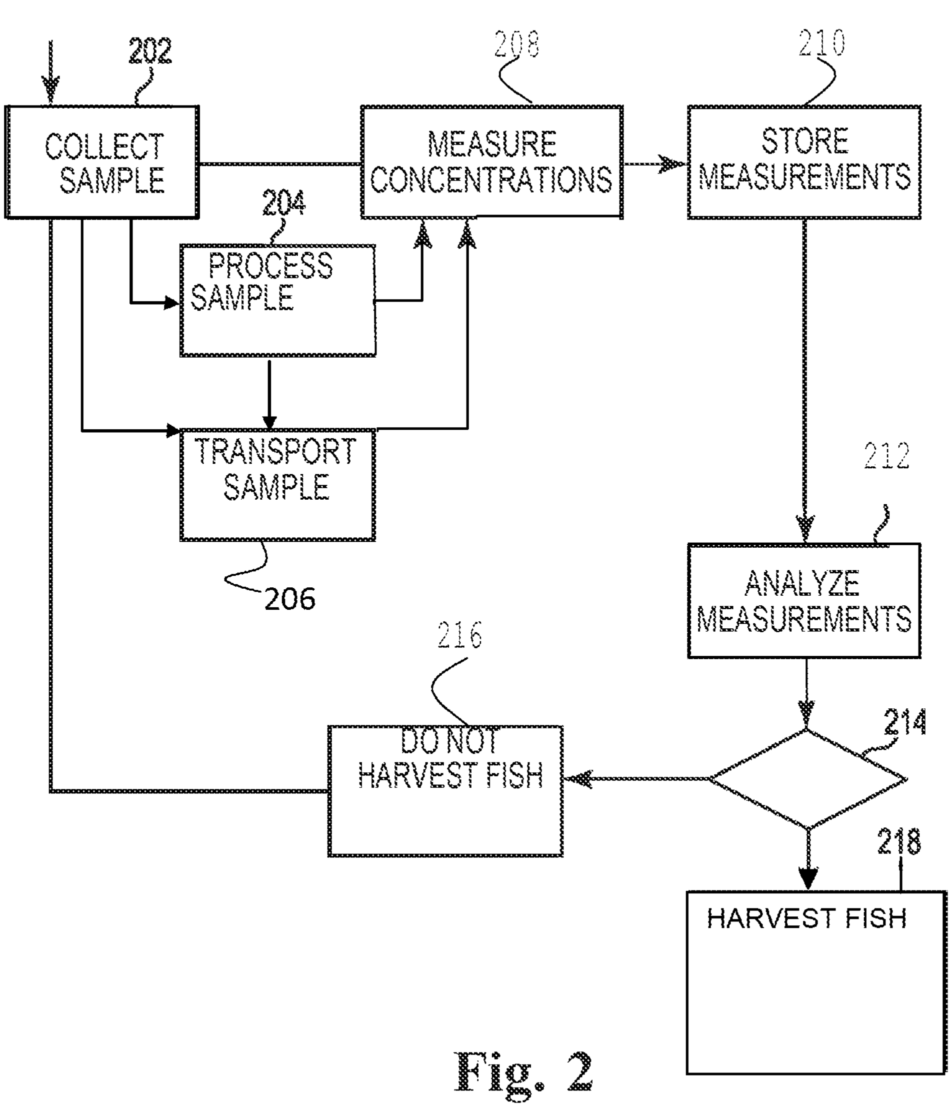
FIG. 2 is a block diagram of a system for sampling and assessing velvet disease presence in water or fish.

A block diagram 200 of steps that may be employed in the disclosed method is shown in FIG. 2. A sample is collected 202 from water or from a subject (e.g., a marine or freshwater fish), and optionally processed 204 to obtain release AO or PP organisms into the sampling solution. The sample is optionally transported 206 to a measurement instrument where measurements are obtained 208 to determine the presence of velvet disease. The measurements are stored 210 along with other previously or subsequently stored measurements for samples from the same population or region, using for example onboard, nearby, networked or cloud storage. The stored measurements are analyzed 212 using for example onboard, nearby, networked or cloud computing. Based on analysis 212, an alternative 214 is followed, namely to delay or forego 216 any introduction of water or fish into a facility or any harvest, transport or sale of fish from such facility for a given time period and to instead continue monitoring or treatment of such fish, or to permit harvest 218, transport, or sale of the fish.

Figures 3, 4:
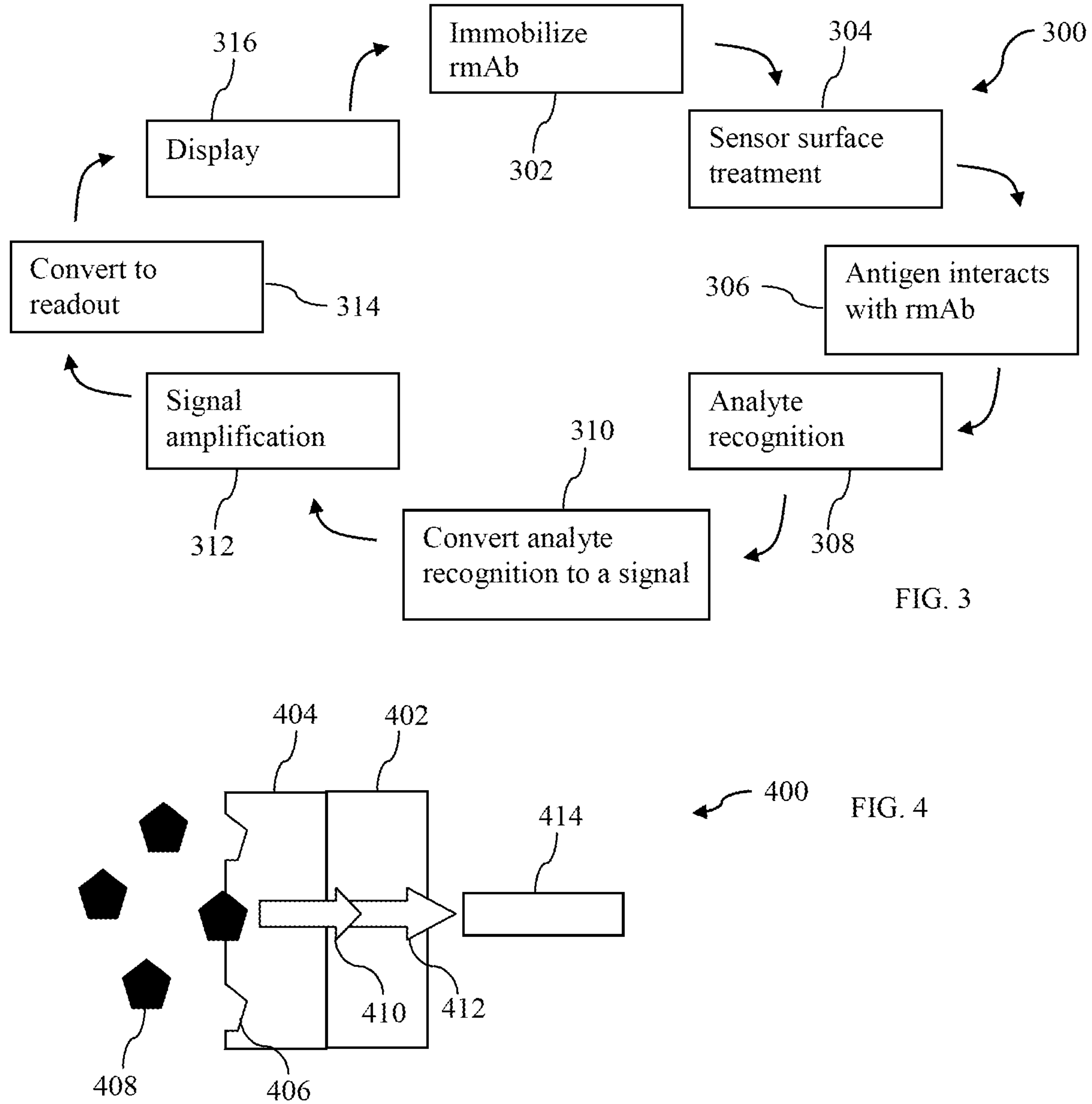
FIG. 3 is a flowchart of a velvet disease RDT biosensor assay device.
FIG. 4 is a block diagram of a velvet disease RDT biosensor assay device in use.

A block diagram 300 demonstrating the general principles of the disclosed RDT biosensor assay device is shown in FIG. 3. A biosensor element, containing one or more conjugated (detection) rmAbs and one or more immobilized (capture) rmAbs that are cross-reactive with one or more AO or PP antigens, is present in the assay device. In one embodiment, the capture rmAbs is immobilized 302 and treated or otherwise applied to the surface of a sensor 304 on a support. The capture rmAbs antibodies may be immobilized on sensor 304 by a measure such as absorption, entrapment, covalent coupling, affinity, the use of binding proteins, chemical binding to polypeptide strands, or any other binding method. The binding method may be selected and configured such that exposure of the paratope is optimized after binding to permit unimpaired antibody-antigen complex formation. In embodiments, the capture rAbs may be self-immobilizing. The conjugated (detection) rmAbs are also bound to the support or are bound to particles that can migrate along the support.

In another embodiment, the conjugated (detection) rmAbs are immobilized on sensor 304 and the capture rmAbs are also bound to the support or are bound to particles that can migrate along the support.

For the various embodiments mentioned above, a target analyte, e.g., a sample containing AO or PP organisms, interacts 306 with the biosensor element (viz., the detection and capture rmAbs) to cause analyte recognition 308 and conversion to a signal by transducer 310. The resulting signal may depend upon the nature of the biosensor employed (e.g., an electrochemical, electronic, optical, piezoelectric, gravimetric, pyroelectric or other suitable biosensor). The signal is amplified 312 and converted to a readout 314, e.g., converted to a numerical output using an algorithm, and the readout is displayed 316. Depending on the needs of the user and the system, the output data 316 may be used as feedback to improve the sensor and improve the selection of the biosensor components 302. Results may also be cross-analyzed for verification with a standard or results from another well-known assay, such as ELISA.

A block diagram 400 demonstrating a detection process for the disclosed biosensor is shown in FIG. 4. A transducer 402 may be prepared for biosensor function by applying a surface treatment 404 containing a mixture 406 (and in some embodiments not shown in FIG. 4, successive layers) of the above-mentioned immobilized or particle-bound detection rmAbs and capture rmAbs. AO or PP organisms 408 interact with the rmAbs 406 producing a bio signal 410 which is converted into an electrical signal 412 by the transducer 402. Transducer 402 may use a variety of physicochemical processes to transform the bio signal 410. For example, transducer 402 may be optical, piezoelectric, electrochemical, electrochemiluminescent, etc. Following amplification and conversion, the signal 412 results in a display output 414.

The disclosed analysis may be performed using a variety of engines, each of which is constructed, programmed, configured, or otherwise adapted, to autonomously carry out a function or set of functions. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine may be realized in a variety of physically realizable configurations, and should generally not be limited to any particular implementation discussed or exemplified herein, unless such limitations are expressly called out. In addition, an engine can itself be composed of more than one sub-engine, each of which can be regarded as an engine in its own right. An engine or a variety of engines may correspond to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically discussed herein.

Various embodiments of the disclosed system, and the corresponding methods of configuring and operating the disclosed system, may be performed using cloud computing, client-server, or other networked environments, or any combination thereof. The components of the system can be located in a singular "cloud" or network, or spread among many clouds or networks. End-user knowledge of the physical location and configuration of components of the system is not required.

As will be readily understood by one of skill in the art, the disclosed system may be implemented using at least one processor and operably coupled memory. The processor can be any programmable device that accepts digital data as input, is configured to process the input according to instructions or algorithms, and provides results as outputs. In an embodiment, a processor can be a central processing unit (CPU) configured to carry out the instructions of a computer program. A processor is therefore configured to perform at least basic arithmetical, logical, and input/output operations.

Memory operably coupled to the processor can include volatile or non-volatile memory as required by the coupled processor to not only provide space to execute the instructions or algorithms, but to provide the space to store the instructions themselves. In embodiments, volatile memory can include random access memory (RAM), dynamic random-access memory (DRAM), or static random-access memory (SRAM), for example. In embodiments, non-volatile memory can include read-only memory, flash memory, ferroelectric RAM, hard disk, floppy disk, magnetic tape, or optical disc storage, for example. The foregoing lists in no way limits the type of memory that can be used, as these embodiments are given only by way of example and are not intended to limit the scope of the disclosed system. The disclosed storage component generally includes electronic storage for data concerning for example the locations, dates, and optionally the times at which samples have been taken and a name, number or other identifier for each sample. In an embodiment, the disclosed storage may be a general-purpose database management storage system (DBMS) or relational DBMS as implemented by, for example, Oracle, IBM DB2, Microsoft SQL Server, PostgreSQL, MySQL, SQLite, Linux, or Unix solutions, and for which SQL calls may be utilized for storage and retrieval. In another embodiment, the disclosed storage, engine or both may employ a cloud computing service such as the Amazon Web Services (AWS) cloud computing service.

The invention is further illustrated in the following non-limiting examples, in which all parts and percentages are by weight unless otherwise indicated.

Example 1

Natural Culturing of AO for Antigen Isolation

A source of antigen (Ag) is necessary for using the HuCAL phage library to select and develop the disclosed rmAbs. To maintain a natural source of AO-Ag (trophont and dinospore) for use in the immunoassays of this project, AO is cultured in a biosecure aquaculture facility under approved protocols and under the supervision of a veterinarian. The culturing of AO with naïve host fish allows for a higher infection intensity and increases the yield of trophonts and dinospores. Culturing of trophont and dinospores is performed according to published methods, using a 500-L tank containing artificial seawater, equipped with appropriate aeration, biofilters and filtration for the culturing of AO. The temperature and salinity are maintained for the desired rearing of AO at 25° C. and 26 ppt respectively. All water quality parameters including DO, temperature, pH, salinity, ammonia and nitrite are monitored daily. Previously AO infected fish obtained from aquaculture facilities are frozen, sent to a lab and examined via microscopy for the presence of AO followed by PCR confirmation. Excised gills from frozen infected fish are used to obtain the trophonts for inoculation of the culture tank. Naïve pinfish (Lagodon rhomboids) obtained from local aquaculture farms are introduced to the inoculated tank and observed until evidence of significant infection is displayed by the fish (air gulping, erratic swimming, side scraping). The fish are removed and their gill arches excised, placed in glass dishes with artificial seawater, and gently agitated to dislodge trophonts. A subsample of seawater with the detached trophonts is passed through a 150 μm mesh filter, and the filtrate centrifuged at 200×g for 10 mins. The trophont pellet is sonicated to disrupt the cellular tissue and stored at −80° C. to be used as a first Ag in HuCAL screening for AO-rmAbs. The remaining excised gill arches are allowed to settle for 20-30 min to allow the trophonts to transform into the tomont phase. The seawater is filtered twice, once with 200 μm and then with a 60 μm filter to remove any material larger than the tomont. The filtered tomonts are washed 3 times with sterile water and placed in 25 ml glass tube along with additional gill material as a substrate and incubated at 22° C. for 72 hours to transform into dinospores. The dinospores are transferred by to a clean centrifuge tube and centrifuged for 10 mins at 200×g to pellet the tissue followed by sonication. The sonicated dinospores are stored at −80° C. for use as a second Ag in HuCAL screening for AO-rmAbs.

Example 2

HuCAL Library Screening for Identification of Two AO-rmAbs

Clownfish immunized with sonicated dinospores were able to generate an immune response that recognized both the dinospore and trophont sonicated antigens (Ags). However, the tomont was not recognized due to rapid encysting which reduced Ag exposure. This suggests that the dinospore and trophont life stages may possess similar Ags allowing for the development of rmAbs having the ability to detect both these infective life stages. Therefore, both free-swimming dinospores (sonicated) and parasitic trophont (sonicated) are used to screen the HuCAL library for AO-rmAbs and create an AO-RDT for monitoring AO on fish bodies and in water. In order to identify AO-rmAbs, guided selection for epitope recognition of the dinospore and trophont Ags is performed. Selection of Abs using HuCAL technology is done in vitro, which enables greater flexibility for Ab generation than conventional methods based on animal immunization. Guided selection strategies involving either blocking steps or the use of two or more Ags are employed for the isolation of epitope-specific Abs, or for Abs that recognize different epitopes of the same Ag. Initial selection involves the presentation of the HuCAL Ab library to the sonicated dinospore immobilized on a solid support. Abs identified by the first round of selection are then presented to the sonicated trophont immobilized on a solid support. Three or more rounds of selection may be performed to enrich the Ab library for specific dinospore and trophont binding. Activity and specificity of the AO-rmAbs are tested using a quality control (QC) ELISA, in which the AO-rmAbs are tested on three non-related standard Ags and on all positive and negative control Ags. A primary criterion for selecting the rmAbs is their ability to detect the whole AO organism at various life stages. The rmAbs that pass all initial tests with the sonicated dinospores and trophonts are then tested with intact dinospores, tomonts, and trophonts as a final selection process.

Example 3

ELISA Testing to Determine AO-rmAbs Pairings, QA and QC

Twenty rmAbs are selected from the HUCAL Library for potential use in an AO-RDT. The RDT employs a lateral flow assay (LFA), based on a sandwich ELISA format that requires two rmAbs, one serving as the "capture" rmAb and the other serving as the "detector" rmAb. Some Abs will work better as the capture and others as the detector. To determine which mAbs work best and as capture or detector, pairing of the rmAbs is performed using several capture or detector combinations and evaluated against traditional ELISA assay tests. The ELISA tests use as positive Ags the whole and sonicated forms of the trophonts and dinospores obtained in Example 1, with phosphate buffered saline (PBS) and bovine serum albumin (BSA) serving as negative controls. For diagnostic purposes, the ELISA and RDT assays are treated as qualitative assays requiring a simple positive or negative response for the presence of AO. For evaluation of a negative response, optical density (OD) measurements obtained from the negative controls are used to determine the upper limit of negativity with a 99.9% confidence limit. A positive response value is set based on the mean OD of the negative controls plus three standard deviations of the mean. Further optimization is performed by comparing and correlating ELISA results of those from conventional microscopy. Twenty or more positive and negative samples analyzed by ELISA are validated by microscopy and PCR for the presence or absence of AO. Once optimized, the ELISA assay is used for at least three independent experiments to determine the reproducibility of the AO-rmAb ELISA assay.

Example 4

ELISA Testing for PP Cross-Reactivity and Species Specificity

To investigate whether rmAbs that target AO may also detect the freshwater parasite PP by cross-reactivity to PP, freshwater fish naturally infested with PP are obtained from a collaborating aquaria facility. The investigation is based upon the shared common phylogeny (class Dinophyceae) of the AO and PP ectoparasites, as well as their morphologic and developmental similarities. Gill microscopy is used to validate the presence of PP with confirmation by PCR through amplification of ribosomal DNA (rDNA). Isolation of the trophonts and dinospores is carried out using the method described in Example 1. The PP trophont and PP dinospore as well as the proteins isolated by sonication from each of the life stages are be tested with AO-rmAb pairs by sandwich ELISA. The criteria employed in Example 3 are used to determine a positive and negative response for the presence of PP. In addition, the AO-rmAbs pairs are evaluated for species specificity to other related and non-related dinoflagellate species.

Example 5

Validation

Before natural culturing of the AO trophont and dinospore for use as Ags as described in Example 1, the gills of the naturally infected fish are excised. Initial identification of the trophont is performed using microscopy, followed by confirmation using highly AO specific PCR detection of the rDNA. Activity and specificity of the AO-rmAbs are tested using a quality control (QC) ELISA, in which the AO-rmAbs are tested on three non-related standard Ags and on the positive and negative control Ags described in Example 2. Sandwich ELISA optimization for the best pairing of capture and detector AO-rmAbs is performed and compared and correlated to the optimized AO-rmAbs pair ELISA results obtained using conventional microscopy to evaluate the presence of AO as described in Example 3. The AO-rmAbs are tested for cross-reactivity with PP to determine utility of the AO-rmAbs as a tool for detection of PP in freshwater fish species. Cross-reactivity of the AO-rmAbs with other dinoflagellates is carried out to determine species specificity as described in Example 4.

Example 6

Data Analysis and Interpretation

In order to compare and correlate results from ELISA, microscopy and PCR, data are correlated and evaluated using linear regression, variance and Spearman rank correlation analyses in R statistics.

Example 7

*Amyloodinium ocellatum* Aptamer Selection

Figure 5:
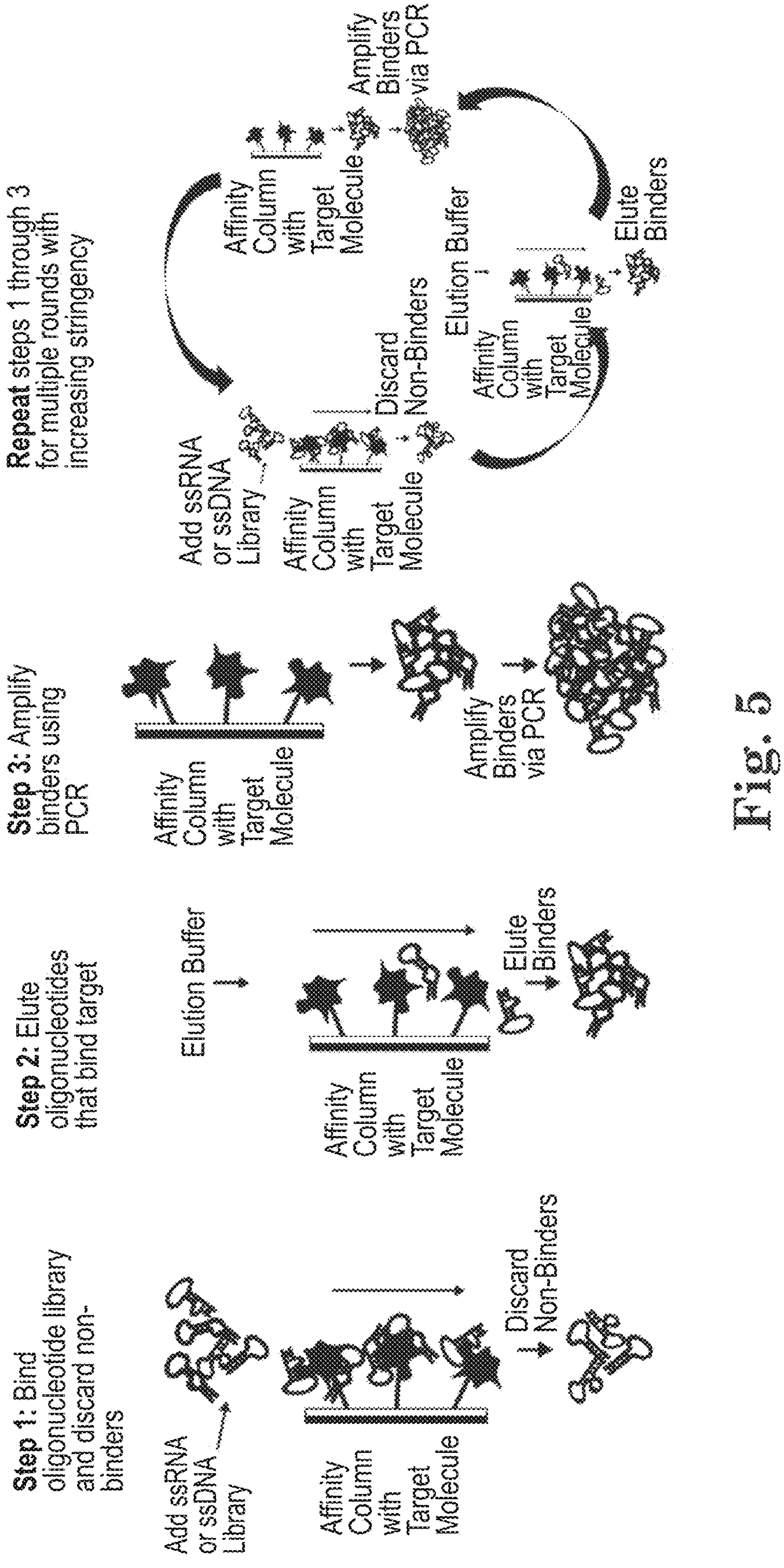
FIG. 5 is a block diagram of an example SELEX process.

In embodiments, aptamers can be used to develop a lateral flow *Amyloodinium ocellatum* (AO) biosensor (aptasensor). Aptamers can be generated using an entirely in vitro process called Systematic Evolution of Ligands by EXponential enrichment (SELEX). The SELEX procedure involves presenting a random DNA library to the target (AO) in multiple rounds of binding, partitioning, recovery, and amplification until the DNA library is fully enriched for binders to the target. FIG. 5 is a block diagram of an example SELEX process.

This highly selective and rigorous process can generate aptamers which may have superior sensitivity and specificity compared to equivalent target protein antibodies. Once a target aptamer sequence is known, it becomes virtually immortalized through chemical synthesis, resulting in minimal to no batch-to-batch variation (a common problem with antibodies). This characteristic confers on aptamers a significant advantage over conventional antibodies in that they can be synthesized with 100%, or nearly 100%, reproducibility. The aptasensor relies on the ability of the aptamer (receptor) to recognize its target of interest (ligand), i.e., *Amyloodinium*. Once identified, the aptamer(s) may be used to create an in situ lateral flow immunoassay for the early detection of the AO dinospore life stage in water samples.

A pure culture of AO dinospores can be used as the target for aptamer selection through the SELEX process. The dinospores immobilized on a Whatman glass fiber membrane can be exposed to an aptamer library (with a starting diversity of approximately $10^{15}$ individual candidate sequences, for example). The library can be added to the membrane in solution and allowed to incubate. The membrane may then be washed to remove non-binding candidates, and the bound candidates eluted from the membrane. The bound candidates can be amplified by polymerase chain reaction (PCR) and converted back to ssDNA to be used as the input library pool for the next round of SELEX. The SELEX can be performed over ten rounds while the stringency is increased, such as by reducing the time allowed for binding or increasing the number of post-binding washes performed. Negative selection can be made using a plain membrane without dinospores, which may ensure that the aptamers are not binding to the filter. At the end of the SELEX, Next-generation Sequencing (NGS) can be performed on the sequence pools, such as from rounds 2, 4, 6, 8, and 10. Using NGS, bioinformatics, or a proprietary method, 24-candidate AO dinospore binding aptamers were identified in an example execution.

Figure 6:
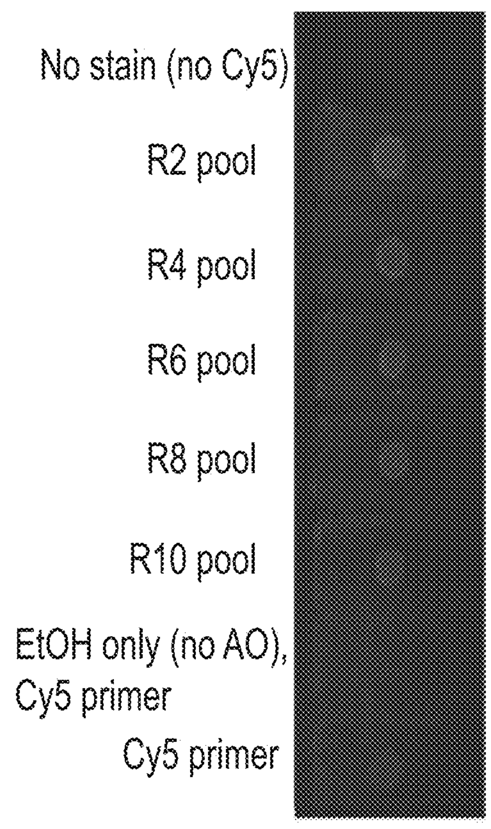
FIG. 6 is an example fluorescence dot blot of AO dinospores immobilized on a PVDF membrane.

A fluorescence dot blot analysis can be performed to visualize aptamer binding to the AO dinospores. FIG. 6 is an example fluorescence dot blot of AO dinospores immobilized on a PVDF membrane. The AO dinospore samples can be loaded on a polyvinylidene fluoride (PVDF) membrane, while the aptamer pools can be fluorescently dyed by amplification with a Cy5-labelled PCR primer. AO samples and aptamer pools can be incubated to stain the dots in separate wells. Stained dots can be scanned for Cy5 fluorescence using a GenePix microarray scanner. An example execution of this analysis may indicate that the aptamers can bind to the AO dinospores, however at or slightly above background, as demonstrated by the intensity of AO/aptamer pool dots compared to the Cy5 primer background dot. A lack of signal in the no stain (no Cy5) well, along with the lack of a visible dot in the EtOH only (no AO), Cy5 primer well can confirm that AO was successfully dotted onto the membrane. Visible dots can also confirm that some staining was achieved.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A device for detecting velvet disease infestation in aquaculture and fishing, the device comprising: a test plate comprising a support bearing at least one conjugated (detection) affinity reagent and at least one immobilized (capture) affinity reagent that are cross-reactive with one or more *Amyloodinium ocellatum* (AO) antigens or *Piscinoodinium pillulare* (PP) antigens, the conjugated affinity reagent and the immobilized affinity reagent being selected to target two infectious life stages of AO, PP, or AO and PP, the conjugated affinity reagent and the immobilized affinity reagent being bound to the support or bound to particles that can migrate along the support.

2. The device of claim 1, wherein the affinity reagents are cross-reactive with one or more AO antigens.

3. The device of claim 1, wherein the affinity reagents are cross-reactive with one or more PP antigens.

4. The device of claim 1, wherein the affinity reagents are cross-reactive with one or more AO antigens and one or more PP antigens.

5. The device of claim 1, wherein the affinity reagents are bound to the support.

6. The device of claim 1, wherein the affinity reagents are bound to particles that can migrate along the support.

7. The device of claim 1, further comprising the support bearing a sample.

8. The device of claim 1, wherein the affinity reagents are aptamers.

9. The device of claim 1, wherein the affinity reagents are rmAbs.

10. The device of claim 1, wherein at least one of the affinity reagents is an aptamer and at least one of the affinity reagents is an rmAb, and wherein the two infectious life stages are the dinospore and trophont life stages.

11. A device for detecting velvet disease infestation in aquaculture and fishing, the device comprising: a test plate comprising a support bearing at least one conjugated (detection) affinity reagent and at least one immobilized (capture) affinity reagent that are cross-reactive with one or more *Amyloodinium ocellatum* (AO) antigens or *Piscinoodinium pillulare* (PP) antigens, the conjugated affinity reagent and the immobilized affinity reagent being selected to target two infectious life stages of AO, PP, or AO and PP, the conjugated affinity reagent and the immobilized affinity reagent being bound to the support or bound to particles that can migrate along the support.

12. The system of claim 11, further comprising:

a processor; and an engine for detecting AO or PP antigens in the sample.

13. The system of claim 12, further comprising storage for a set of sample locations, sample dates, and detected velvet disease antigen presence in the samples.

14. The system of claim 11, wherein the affinity reagents are aptamers.

15. The system of claim 11, wherein the affinity reagents are rmAbs.

16. The system of claim 11, wherein at least of the affinity reagents is an aptamer and at least one of the affinity reagents is an rmAb, and wherein the two infectious life stages are the dinospore and trophont life stages.

17. A device for detecting velvet disease infestation in aquaculture and fishing, the device comprising: a test plate comprising a support bearing at least one conjugated (detection) affinity reagent and at least one immobilized (capture) affinity reagent that are cross-reactive with one or more *Amyloodinium ocellatum* (AO) antigens or *Piscinoodinium pillulare* (PP) antigens, the conjugated affinity reagent and the immobilized affinity reagent being selected to target two infectious life stages of AO, PP, or AO and PP, the conjugated affinity reagent and the immobilized affinity reagent being bound to the support or bound to particles that can migrate along the support.

18. The method of claim 17, wherein the affinity reagents are aptamers.

19. The method of claim 17, wherein the affinity reagents are rmAbs.

20. The method of claim 17, wherein at least one of the affinity reagents is an aptamer and at least one of the affinity reagents is an rmAb, and wherein the two infectious life stages are the dinospore and trophont life stages.

* * * * *